United States Patent [19]
Call et al.

[11] Patent Number: 5,350,840
[45] Date of Patent: Sep. 27, 1994

[54] LOCALIZATION AND CHARACTERIZATION OF THE WILMS' TUMOR GENE

[75] Inventors: Katherine M. Call, Malden; Thomas M. Glaser, Cambridge, both of Mass.; Caryn Y. Ito, Cerrboro, N.C.; Alan J. Buckler, Brookline, Mass.; Jerry Pelletier, Cambridge, Mass.; Daniel A. Haber, Cambridge, Mass.; Elise A. Rose, Emeryville, Calif.; David E. Housman, Newton, Mass.

[73] Assignee: Massachusetts Institute of Technology, Cambridge, Mass.

[21] Appl. No.: 795,323

[22] Filed: Nov. 20, 1991

Related U.S. Application Data

[63] Continuation of Ser. No. 435,780, Nov. 13, 1989, abandoned.

[51] Int. Cl.$^5$ .................... C07H 21/02; C07H 21/04; C12Q 1/68
[52] U.S. Cl. ...................... 536/23.1; 435/6; 935/77; 935/78; 536/24.31
[58] Field of Search .................. 536/26–29, 536/23.1, 24.31; 435/6; 935/77, 78

[56] References Cited

FOREIGN PATENT DOCUMENTS 91901084 8/1992 European Pat. Off. .
9006629 11/1990 PCT Int'l Appl. .

OTHER PUBLICATIONS

Gessler, M. et al., "Homozygous deletion in Wilms tumours of a zinc-finger gene identified by chromosome jumping", Nature, 343: 774–778 (1990).
Gessler, M., et al., "Molecular Mapping and Cloning of the Breakpoints of a Chromosome 11p14.1-p13 Deletion Associated with the AGR Syndrome" Genomics, 3(2): 117–123 (1988).
Call, K. M. et al., Cell, 60:509–520 (1990).
Davis, L. M. et al., Science, 241:840–842 (1988).
Francke, U. et al., Cytogenet. Cell Genet., 24:185–192 (1979).
Francke, U., Nature, 343:692–694 (1990).
Gessler, M. et al., Science, 244:1575–1578 (1989).
Glaser, T. et al., Nature, 321:882–887 (1986).
Hoffman, M., Science, 246:4936 (1989).
Junien, C. et al., Cancer Genetics and Cytogenetics, 10:51–57 (1983).
Kolata, G. B., Science, 207:970–971 (1980).
Koufos, A. et al., Am. J. Hum. Genet., 44:711–719 (1989).
Knudson, A. G. and Strong, L. C., J. Natl. Can. Inst., 48(2):313–324 (1972).
Lavedan, P. et al., Cytogenet. Cell. Genet., 50:70–74 (1989).
Matsunaga, E., Human Genetics, 57:231–246 (1981).
Porteous, D. J. et al., Proc. Natl. Acad. Sci. USA, 84:5355–5359 (1987).
Riccardi, V. M. et al., Pediatrics, 61:604–610 (1978).
Yunis, J. J. and Ramsay, N. K. C., J. Pediatrics, 96:1027–1030 (1980).
Compton et al., Cell 55:827–836 (Dec. 2, 1988).
Lewis et al., Genomics 3:25–31 (1988).

Primary Examiner—Stephanie W. Zitomer
Attorney, Agent, or Firm—Hamilton, Brook, Smith & Reynolds

[57] ABSTRACT

The Wilms' tumor gene associated with the 11p13 locus on the human chromosome, as well as a method of analyzing cells for the gene is described and characterized. The gene encodes a transcription unit approximately 50 kb in size and a mRNA of approximately 3 kb, which is expressed in a limited number of cell types (e.g., predominantly kidney cells and ja subset of hematopoietic cells). The polypeptide encoded by the Wilms' tumor DNA includes four "zinc fingers" and a region rich in proline and glutamine, suggesting that the polypeptide has a role in transcription regulation.

8 Claims, 11 Drawing Sheets

```
  1 GAGGAGCAGTGCCTGAGCGCCTTCACTGTCCACTTTTCCGGCCAGTTCACTGGCACAGCC
  1   Q  E  Q  C  L  S  A  F  T  V  H  F  S  G  Q  F  T  G  T  A
 61 GGAGCCTGTCGCTACGGGCCCTTCGGTCCTCCTCCGCCCAGCCAGGCGTCATCCGGCCAG
 21   G  A  C  R  Y  G [P] F  G [P  P  P] S  Q  A  S  S  G  Q
121 GCCAGGATGTTTCCTAACGCGCCCTACCTGCCCAGCTGCCTCGAGAGCCAGCCCGCTATT
 41   A  R  M  F [P] N  A [P] Y  L  P  S  C  L  E  S  Q [P] A  I
181 CGCAATCAGGGTTACAGCACGGTCACCTTCGACGGGACGCCCAGCTACGGTCACACGCCC
 61   R  N  Q  G  Y  S  T  V  T  F  D  G  T [P] S  Y  G  H  T [P]
241 TCGCACCATGCGGCGCAGTTCCCCAACCACTCATTCAAGCATGAGGATCCCATGGGCCAG
 81   S  H  H  A  A  Q  F [P] N  H  S  F  K  H  E  D [P] M  G  Q
301 CAGGGCTCGCTGGGTGAGCAGCAGTACTCGGTGCCGCCCCCGGTCTATGGCTGCCACACC
101   Q  G  S  L  G  E  Q  Q  Y  S  V [P  P  P] V  Y  G  C  H  T
361 CCCACCGACAGCTGCACCGGCAGCCAGGCTTTGCTGCTGAGGACGCCCTACAGCAGTGAC
121   P  T  D  S  C  T  G  S  Q  A  L  L  R  T [P] Y  S  S  D
421 AATTTATACCAAATGACATCCCAGCTTGAATGCATGACCTGGAATCAGATGAACTTAGGA
141   L     Q  M  T  S  Q  L  E  C  M  T  W  N  Q  M  N  L  G
481 GCCACCTTAAAGGGCCACAGCACAGGGTACGAGAGCGATAACCACACAACGCCCATCCTC
161   A  T  L  K  G  H  S  T  G  Y  E  S  D  N  H  T  T  P  I  L
541 TGCGGAGCCCAATACAGAATACACACGCACGGTGTCTTCAGAGGCATTCAGGATGTGCGA
181   C  G  A  Q  Y  R  I  H  T  H  G  V  F  R  G  I  Q     V  R
601 CGTGTGCCTGGAGTAGCCCCGACTCTTGTACGGTCGGCATCTGAGACCAGTGAGAAACGC
201   R  V  P  G  V  A  P  T  L  V  R  S  A  S  E  T  S  E  K  R
661 CCCTTCATGTGTGCTTACCCAGGCTGCAATAAGAGATATTTTAAGCTGTCCCACTTACAG
221   P  F  M  C  A  Y  P  G  C  N  K  R  Y  F  K  L  S  H  L  Q
721 ATGCACAGCAGGAAGCACACTGGTGAGAAACCATACCAGTGTGACTTCAAGGACTGTGAA
241   M  H  S  R  K  H  I  G  E  K  P  Y  Q  C  D  F  K  D  C  E
781 CGAAGGTTTTTTCGTTCAGACCAGCTCAAAAGACACCAAAGGAGACATACAGGTGTGAAA
261   R  R  F  F  R  S  D  Q  L  K  R  H  Q  R  R  H  T  G  V  K
841 CCATTCCAGTGTAAAACTTGTCAGCGAAAGTTCTCCCGGTCCGACCACCTGAAGACCCAC
281   P  F  Q  C  L  C  Q  R  K  F  S  R  S  N  H  L  K  T  H
901 ACCAGGACTCATACAGGTGAAAAGCCCTTCAGCTGTCGGTGGCCAAGTTGTCAGAAAAAG
301   T  R  T  H  I  G  Q  K  P  F  S  C  R  W  P  S  C  Q  K  K
961 TTTGCCCGGTCAGATGAATTAGTCCGCCATCACAACATGCATCAGAGAAACATGACCAAA
321   F  A  R  S  D  E  L  V  R  H  H  N  M  H  Q  R  N  M  T  K
1021 CTCCAGCTGGCGCTTTGAGGGGTCTCCCTCGGGGACCGTTCAGTGTCCCAGGCAGCACAG
341   L  Q  L  A  L
1081 TGTGTGAACTGCTTTCAAGTCTGACTCTCCACTCCTCCTCACTAAAAAGGAAACTTCAGT
1141 TGATCTTCTTCATCCAACTTCCAAGACAAGATACCGGTGCTTCTGGAAACTACCAGGTGT
1201 GCCTGGAAGAGTTGGTCTCTGCCCTGCCTACTTTTAGTTGACTCACAGGCCCTGGAGAAG
1261 CAGCTAACAATGTCTGGTTAGTTAAAAGCCCATTGCCATTTGGTGTGGATTTTCTACTGT
1321 AAGAAGAGCCATAGCTGATCATGTCCCCCTGACCCTTCCCTTCTTTTTTTATGCTCGTTT
1381 TCGCTGGGGATGGAATTATTGTACCATTTTCTATCATGGAATATTTATAGGCCAGGGCAT
1441 GTGTATGTGTCTGCTAATGTAAACTTTGTCATGGTTTCCATTTACTAACAGCAACAGCAA
1501 GAAATAAATCAGAGAGCAAGGCATCGGGGGTGAATCTTGTCTAACATTCCCGAGGTCAGC
1561 CAGGCTGCTAACCTGGAAAGCAGGATGTAGTTCTGCCAGGCAACTTTTAAAGCTCATGCA
1621 TTTCAAGCAGCTGAAGAAAAAATCAGAACTAACCAGTACCTCTGTATAGAAATCTAAAAG
1681 AATTTTACCATTCAGTTAATTCAATGTGAACACTGGCACACTGCTCTTAAGAAACTATGA
1741 AGATCTGAGATTTTTTGTGTATGTTTTTGACTCTTTTGAGTGGTAATCATATGTGTCTT
1801 TATAGATGTACATACCTCCTTGCACAAATGGAGGGGAATTCATTTTCATCACTGGGAGTG
1861 TCCTTAGTGTATAAAAACCATGCTGGTATATGGCTTCAAGTTGTAAAAATGAAAGTGACT
1921 TTAAAAGAAAATAGGGGATGGTCCAGGATCTCCACTGATAAGACTGTTTTTAAGTAACTT
1981 AAGGACCTTTGGGTCTACAAGTATATGTGAAAAAATGAGACTTACTGGGTGAGGAAATC
2041 CATTGTTTAAAGATGGTCGTGTGTGTGTGTGTGTGTGTGTGTGTTGTGTTTGTGTTT
2101 TGTTTTTTAAGGGAGGGAATTTATTATTTACCGTTGCTTGAAATTACTGTGTAAATATAT
2161 GTCTGATAATGATTTGCTCTTTGACAACTAAAATTAGGACTGTATAAGTACTAGATGCAT
2221 CACTGGGTGTTGATCTTACAAGATATTGATGATAACACTTAAAATTGTAACCTGCATTTT
2281 TCACTTTGCTCTCAATTAAAGTCTATTCAAAA
```

| | | | | | | | | | | | | | |
|---|---|---|---|---|---|---|---|---|---|---|---|---|---|
| Zn++ Finger Consensus | TG E KPY<br>R F<br>— — | X | C | XXXX | C | XXX | F | XXXXX | L | XX | H | XXX | H |
| WT33 | RPF | M | C | AYPG | C | NKRY | F | KLSH— | L | QM | H | SRK | H |
| EGR1 #1 | PH E RPY | A | C | PVES | C | NRR— | F | SRSDE | L | TR— | H | IRI— | H |
| WT33 #1 | TG E KPY | Q | C | DFKD | C | ERR— | F | SRSDQ* | L | KR— | H | QRR— | H |
| EGR2 #1 | VH Q RPY | P | C | PAQG | C | NRR— | F | SRSDQ | L | TR— | H | IRI— | H |
| EGR1 #2 | TG Q KPF | Q—Q—Q | C | ———RI | C | MRN— | F | SRSDH | L | TT— | H | IRT— | H |
| WT33 #2 | TG V KPF | | C | ———LT | C | QRK— | F | SRSNH | L | KT— | H | TRT— | H |
| EGR2 #2 | TG H KPF | | C | ———RI | C | MRN— | F | SRSDQ | L | TT— | H | IRT— | H |
| EGR1 #3 | TG E KPF | A | C | ———DI | C | GRK— | F | ARSDE | R | KR— | H | TKI | H |
| WT33 #4 | TG Q—Q KPF | S | C | RWPS | C | QKK— | F | ARSDE | L | VR— | H | HNM | H |
| EGR2 #3 | TG KPF | A | C | ———DY | C | GRK— | F | ARSDE | R' | KR | H | TKI | H |

LOCALIZATION AND CHARACTERIZATION OF THE WILMS' TUMOR GENE

This is a continuation of application Ser. No. 435,780, filed Nov. 13, 1989 now abandoned

BACKGROUND

Wilm's tumor (WT) is an embryonal malignacy of the kidney which affects approximately 1 in 10,000 infants and young children. Matsunaga, *Human Genetics*, 57: 231–246 (1981). The molecular basis of Wilms' tumor is not well understood.

A subset of Wilms' tumor cases (approximately 2%) occur in association with aniridia (AN2), a defect in the development of the iris, as well as urogenital abnormalities and mental retardation. Miller et al., *New Engl. J. Med.*, 227:922–927 (1964). These disorders form the WAGR syndrome, and can be attributed to constitutional deletions of DNA in band 11p13 on human chromosome 11 in a group of genes known as the WAGR complex. Riccardi et al., *Pediatrics*, 61:604–610 (1978); Francke, et al., *Cytogenet. Cell Genet.*, 24:185–192 (1979). In these cases, bilateral Wilms' tumors are frequently observed, as are dysplastic changes in surrounding renal tissue (nephroblastomatosis) which are thought to precede malignant transformation. Bove and McAdams, *Perspectives on Pediatric Pathol.*, 3:185–223 (1976). As a recessive oncogene or anti-oncogene, the Wilms' tumor locus curtails the growth of undifferentiated nephretic cells. It conforms generally to a two-mutation model of carcinogenesis and is genetically similar to the retinoblastoma locus on chromosome 13 q. These observations lead to the conclusion that at least in this subset of Wilms' tumors, the inactivation of a gene in 11p13, analogous to the retinoblastoma (RB) gene, is a key event in tumor formation. Considerable effort has been expended in attempting to localize the gene responsible for WT, as is evidenced by the numerous reports describing such efforts. For example, genomic analysis of sporadic Wilms' tumors showing loss of heterozygosity at polymorphic loci supports the localization of Wilms' tumor gene to 11p13. Koufos et al., *Nature*, 309:170–172 (1984); Orkin et al., *Nature*, 309:172–174 (1984); Reeve et al., *Nature*, 309:174–176 (1984); Fearon et al., *Nature*, 309:176–178 (1984).

Based on additional research, it appears that Wilms' tumor may be caused by loss of function at alternative loci. In studies of two families showing hereditary predisposition to Wilms' tumor, linkage to 11p genetic markers was excluded, indicating the presence of at least one additional Wilms' tumor locus. Grundy et al., *Nature*, 336:374–376 (1988): Huff et al., *Nature*, 336:377–378 (1988). Further studies showed loss of heterozygosity in Wilms' tumors at 11p15 rather than 11p13. Reeve et al., *Mol. Cell Biol.*, 9:1799–1803 (1989); Koufos et al., *am. J. Hum. Gen.*, 44:711–719 (1989). Although these data suggest the possibility of additional loci, the 11p13 Wilms' tumor locus is clearly associated with constitutional WAGR deletions and somatic chromosome rearrangements in a subset of sporadic tumors. Lewis et al., *Genomics*, 3:25–31 (1988).

Despite considerable interest in identifying the Wilms' tumor gene and work focusing on doing so, to the present time, a transcript mapping to the region identified as containing the Wilm's tumor gene has not been identified.

SUMMARY OF THE INVENTION

The present invention relates to a method of analyzing cells for the Wilms' tumor gene, as well as to a method of analyzing cells for the Wilms' tumor gene transcript or the encoded polypeptides. As used herein, the term Wilms' tumor gene or Wilms' tumor DNA refers to lesions in chromosome 11 band 13 (11p13) which are characteristic of WAGR or Wilms' tumor, (i.e., found in cells affected in these conditions), but which can reasonably be expected to be associated with or causative of other tumor types. The present invention further relates to DNA sequences, both genomic and cDNA clones, which map within the boundaries of constitutional and tumor deletions which define the Wilms' tumor locus on human chromosome 11 band p13 (11p13). For the first time, a transcript which maps to the region containing the Wilms' tumor gene has been identified. The transcript has been characterized and shown to span approximately 50 kb and to encode an mRNA (referred to as WT mRNA) approximately 3 kb in length. The WT mRNA has been shown to be expressed in a limited number of cell types (i.e., predominantly kidney cells and a subset of hematopoietic cells).

The amino acid sequence of the polypeptide encoded by the sequence has also been derived and features of the polypeptide have been examined. Several of these features, such as the presence of four zinc finger domains and of a region rich in proline and glutamine, are indicative of a role in transcription regulation. The localization of the gene to 11p13, its tissue-specific expression and its predicted function, support the conclusion that it is the 11p13 Wilms' tumor gene. The present invention includes a method of identifying the Wilms' tumor gene; the isolated Wilms' tumor gene, the isolated gene transcript; the isolated encoded polypeptide; and diagnostic methods and reagents based thereon. The present invention makes available for the first time a method of identifying in a sample DNA which is clearly within the 11p13 Wilms' tumor locus, an mRNA transcript thereof or a Wilms' tumor-encoded polypeptide, as well as materials (e.g., nucleic acid probes, anti-Wilms' tumor polypeptide antibodies) useful in the method. This is particularly valuable because although Wilms' tumor is highly malignant and grows rapidly, it represents one of the clearest examples of success in pediatric oncology, as a result of the development of effective therapeutic regimens. The present invention provides a means by which the risk of developing WAGR or Wilms' tumor can be assessed prior to its appearance and the presence of the disease, once it has occurred, can be confirmed, thus making it possible to intervene therapeutically prior to or at an early stage in the development of the disease. It also provides a method by which the occurrence of DNA of the same or similar sequence as the Wilms' tumor gene can be detected in other tumor types (e.g., leukemia cells, testicular tumors), using DNA probes or antibodies specific for Wilms' tumor gene-encoded polypeptide.

BRIEF DESCRIPTION OF THE FIGURES

FIG. 3 shows the nucleotide sequence of WT33 cDNA and the predicted amino acid sequence of the open reading frame extending from nucleotide 1 to 1035. The proline and glutamine residues in the proline/glutamine rich region (nucleotides 6 to 468) are boxed and the amino acids of the four zinc fingers (nucleotides 670 to 1002) which fit the zinc finger consensus are underlined.

FIG. 5 is a schematic map showing a comparison of the sequence derived from WT33 to the zinc finger consensus region and the sequences of human EGR1 and EGR2 genes. FIG. 6 shows the results of Southern blot analyses of hybridization of Wilms' tumor cDNA with various DNA.

FIG. 8 shows the results of Northern blot analyses of the expression of WT33 in various tissues and tumor cell lines.

DETAILED DESCRIPTION OF THE INVENTION

Figure 1:
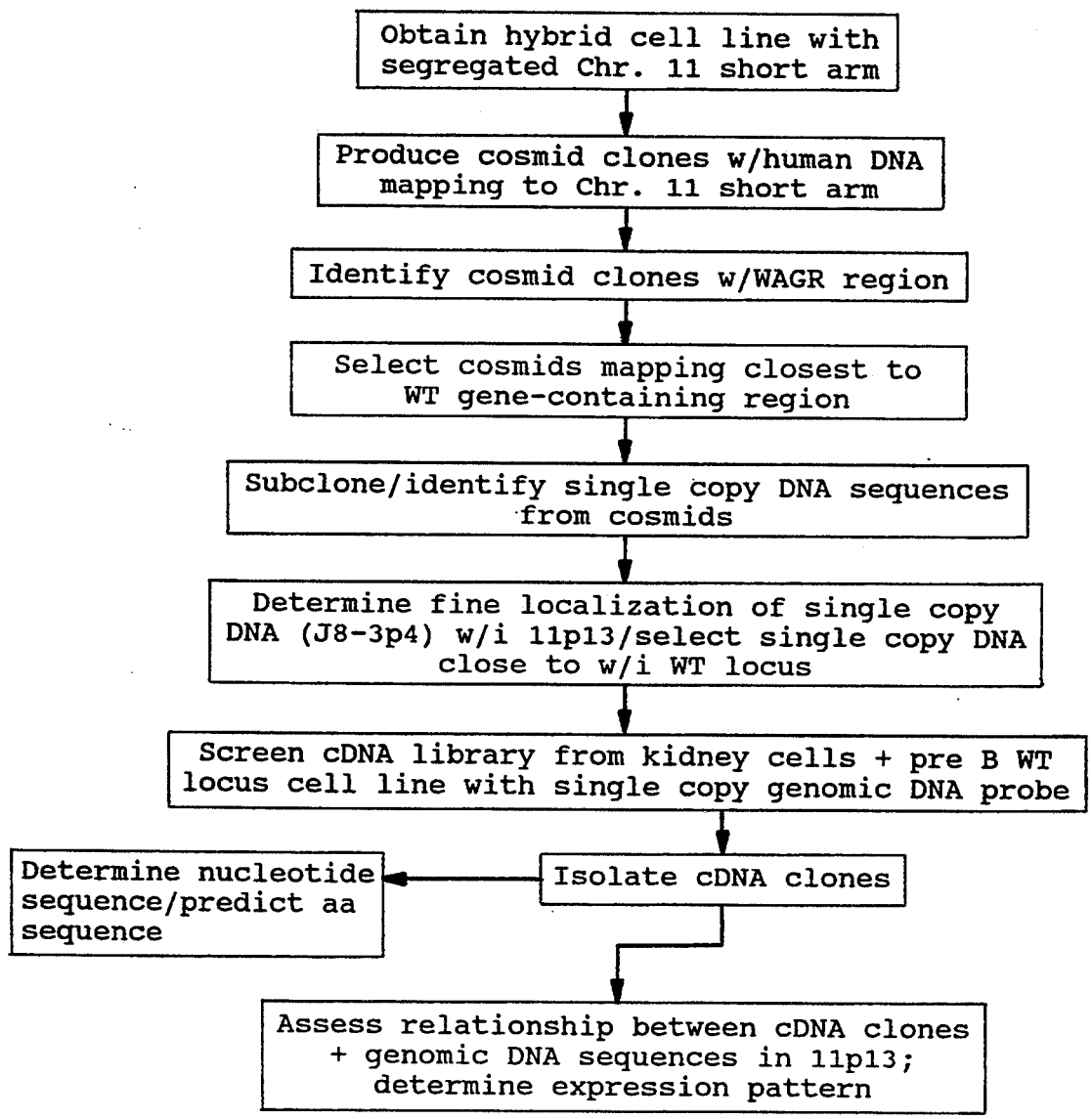
FIG. 1 is a schematic representation of isolation and characterization of the Wilms' tumor gene.

The present invention is based on the identification and characterization of the Wilms' tumor gene and the mRNA transcript of the gene, as well as on the characterization of the polypeptide encoded by the Wilms' tumor gene. As described in detail below, a series of genomic and cDNA clones map within the boundaries of constitutional and tumor deletions which define the Wilms' tumor locus on chromosome 11 band p13 (11p13) have been isolated and characterized. As also described below, the expression pattern of mRNA encoded by the transcription unit which corresponds to the clones has been determined. In addition, the polypeptide encoded by the Wilms' tumor locus has been characterized and shown to have several features which suggest it has a role in the regulation of transcription.

Based on the work described herein, a method of determining the presence or absence of Wilm's tumor DNA, as well as quantitating Wilms' tumor DNA in cells has been developed. Nucleic acid probes which hybridize to Wilms' tumor DNA and nucleic acid probes which hybridize to transcripts of the Wilms' tumor DNA have also been produced and used in the method. Although it is referred to herein as the Wilms' tumor gene or Wilms' tumor DNA, the locus on Chromosome 11 band 13 is referred to in this manner for convenience and is not meant to limit the present invention to WAGR and Wilms' tumor only. That is it is reasonable to expect that the 11p13 locus referred to as Wilms' tumor DNA occurs in (is associated with or causative of) other tumor types, such as leukemia cells and testicular tumors. The present invention is intended to include such an occurrence and provides a method by which the equivalent gene or DNA sequence (i.e., a DNA sequence which cross hybridizes with a probe as described herein and acts as a recessive oncogene or anti-oncogene in cells in which it occurs) can be identified in other types of tumors.

The following is a description of isolation and characterization of Wilms' tumor genomic DNA and cDNA, the mRNA transcript and the encoded polypeptide.

Molecular mapping experiments have narrowed the WAGR regions to a specific interval in 11p13 bounded by the genes encoding erythrocyte catalase (CAT) and the $\beta$ subunit of follicle stimulating hormone (FSHB). Junien et al., *Am. Genet.*, 23:16–168 (1980); van Heyningen et al., *Proc. Natl. Acad. Sci. (USA)*, 82:8592–8596 (1985); Glaser et al., *Nature*, 321:882–887 (1986); Porteous et al., *Proc. Natl. Acad. Sci. USA*, 84:5355–5359 (1987); Watkins et al., DNA, 6:205–212 (1987). Three complementary strategies have been used to further delineate the location of genes within the WAGR region: somatic cell genetics, molecular cloning and pulsed field gel electrophoresis. Somatic cell hybrids segregating specific translocation and deletion chromosomes have been valuable reagents for resolving and defining the position of individual genes within the WAGR region. A substantial number of additional 11p13 DNA markers have been isolated and characterized from chromosome 11-specific DNA libraries. Lewis et al., ibid (1988); Compton et al., *Cell*, 55:827–836 (1988); Davis et al., *Genomics*, 3:24–27 (1988a); Davis et al., *Science*, 241:840–842 (1988b); Gessler et al., *J. Am. Hum. Genet.*, 44:486–495 (1989a); Gessler et al., *Science*, 244:1575–1572 (1989b). Long range restriction maps constructed by pulsed field gel electrophoresis define relatively large intervals for several of the WAGR disease genes.

The method by which Wilms' tumor DNA was isolated is represented schematically in FIG. 1. Initially, a hamster-somatic human cell line (J1-11), in which the short arm of human chromosome 11 had been segregated from the remainder of the human genome, was used to produce cosmid libraries, as described in the Exemplification. One hundred nineteen cosmid clones, all containing human DNA which mapped to the short arm of chromosome 11, were isolated from the library. Clones containing the WAGR region were subsequently identified, using a mapping panel of somatic cell hybrids containing different fragments of human chromosome 11p. Glaser, T. et al., *Som. Cell and Mol. Gen.*, in press (1989). Of the clones isolated in this manner, three (J7-18, J8-3 and J10-15) appeared to map most closely to the region containing the Wilms' tumor gene. The restriction maps of J8-3 and J10-15 showed substantial overlap and, therefore, only one of these cosmids (J8-3) was analyzed further.

Figure 2:
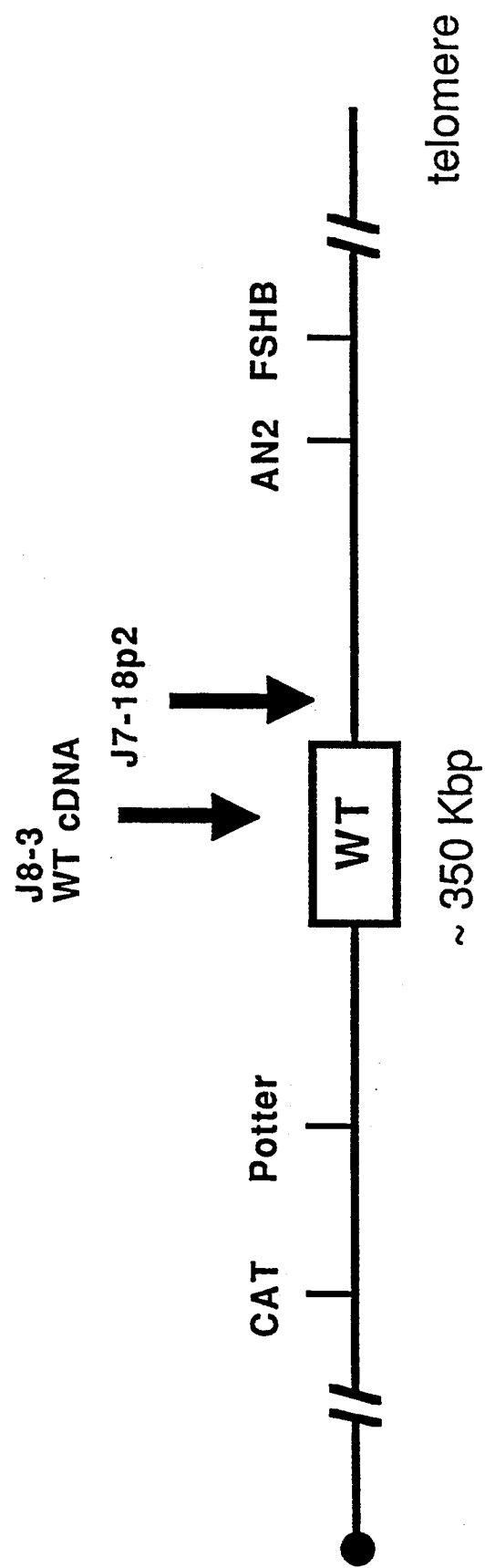
FIG. 2 is a schematic representation of the WAGR region showing the map positions of single copy probes J7-18p2, J8-3p4 and cDNAs homologous to J8-3.

Single copy sequences, designated J7-18p2 and J8-3p4, were subcloned and identified from cosmids J7-18 and J8-3, respectively. The fine localization of these single copy DNA sequences was determined by hybridization to a series of somatic cell hybrids derived from patients with translocations and deletions which define specific intervals within the WAGR region. This is described in detail in the Exemplification and a map summarizing the findings is shown in FIG. 2.

J8-3p4 was used as a probe to screen cDNA libraries. J8-3p4 was selected for this purpose because its map position indicated that it was close to or within the Wilms' tumor locus. In addition, as explained in the Exemplification, two observations suggested that J8-3p4 contained a portion of a transcription unit. A cDNA library derived from human embryonic kidney (HEK) cells was screened with J8-3p4. On the basis of Northern blotting results (see the Exemplification), a human adult kidney library and a human pre B cell library were also screened. Four cDNA clones from these three libraries were studied in detail: two from HEK (WT4, WT2), one from human adult kidney (WT22) and one from a pre B cell line (WT33). Another homologous cDNA clone (WT13) was isolated from the HEK library, using an independently isolated conserved genomic DNA clone, λk13. Glaser, T., The fine structure and evolution of the eleventh human chromosome. Ph.D. thesis, Massachusetts Insititue of Technology, Cambridge, Mass. (1988).

cDNA clone WT33 is 2313 base pairs (bp) in length and the longest clone isolated. It extends the furthest in both the 5' and the 3' directions of the clones isolated. The other four cDNAs share a common internal region of DNA sequence approximately 1000 to 1200 bp in length.

cDNA clone WT33 was selected for further analysis, which is described in detail in the Exemplification. The WT33 nucleotide sequence was determined and the predicted amino acid sequence was derived. Both are represented in FIG. 3. Sequence analysis showed the presence of a continuous open reading frame of 345 amino acids, which extends from nucleotides 1 to 1035. This open reading frame appears to represent most of the WT33 coding segment, but it does not appear to include the initiator methionine codon. Primer extension experiments suggest that an additional 200 bp are present at the 5' end of the mRNA corresponding to WT33. The transcription pattern of the locus corresponding to these cDNAs exhibits some complexity. Experiments utilizing RNA PCR (polymerase chain reaction) indicate variation in mRNA sequence in the 5' segment of the coding region of the mRNA, suggesting alternative splicing patterns among various tissue types.

Of particular interest is that nucleotides 670 to 1002 encode four contiguous "zinc finger" domains. All four zinc fingers encoded by WT33 (FIG. 5) fit the consensus sequence for zinc fingers (Miller, J. et al., EMBO J., 4:1609–614 (1985); Evans, R. N. and S. M. Hollenberg, Cell, 52:1-3 (1988). The H/C link between zinc fingers, typified by the amino acid sequence TGE-R/K-P-F/Y-X, is also conserved in the deduced amino acid sequence. Shuh, R. et al., Cell, 47:1025–1032 (1986).

A search of other polypeptides for sequences related to WT33 revealed a 51% similarity between the amino acid sequence of the zinc finger region of two recently identified human early growth response genes, EGR1, Sukhatme et al., Cell, 53:37–43 (1988) and EGR2, Joseph et al., Proc. Nat's. Acad. Sci. USA, 85:7164–7168 (1988). The early growth response genes have been suggested to be involved in pathways controlling cell proliferation. The individual zinc fingers of WT33 are aligned with the zinc finger consensus sequence and compared with the zinc fingers of EGR1 and EGR2 in FIG. 5. Although the WT33 polypeptide has homology to zinc fingers in other proteins, including TFIIIA and Sp1, the degree of homology is greatest with EGR1 and EGR2 and moreover was observed throughout all three contiguous zinc fingers.

The amino acid content of the region 5' amino terminal to the zinc finger domain is also characteristic of proteins thought to be transcription factors. From the amino terminus to the start of the first zinc finger, there is a high concentration of serine (10.2%), proline (9.8%), glycine (9.7%), threonine (8.8%) and glutamine (7.9%) residues. These amino acids are also highly represented in the amino termini of the polypeptides encoded by EGR1 and EGR2. Proline and glutamine rich domains have been identified as motifs in a number of transcription factors and putative transcription factors. Mitchell and Tjian, Science, 245:371–378 (1989). A high threonine and serine content is also observed in several transcription factors, including Sp1. Courey and Tjian, Cell, 55:887–898 (1988).

Figure 6A:
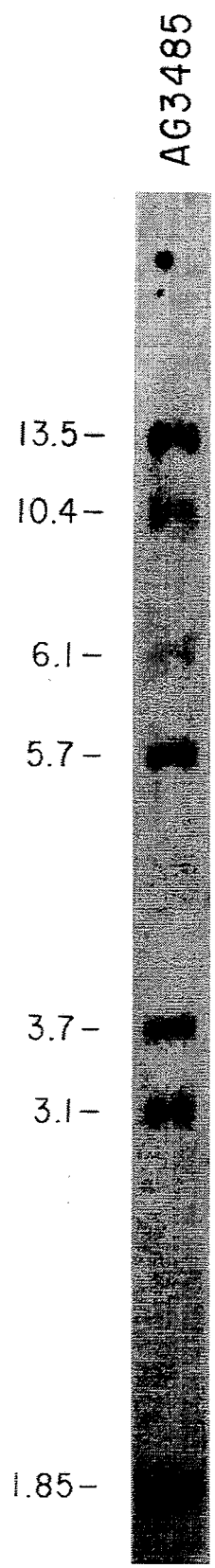
FIG. 6A shows the results of Southern blot analysis of EcoRI digested human lymphoblast DNA hybridized with WT33.
Figure 6B:
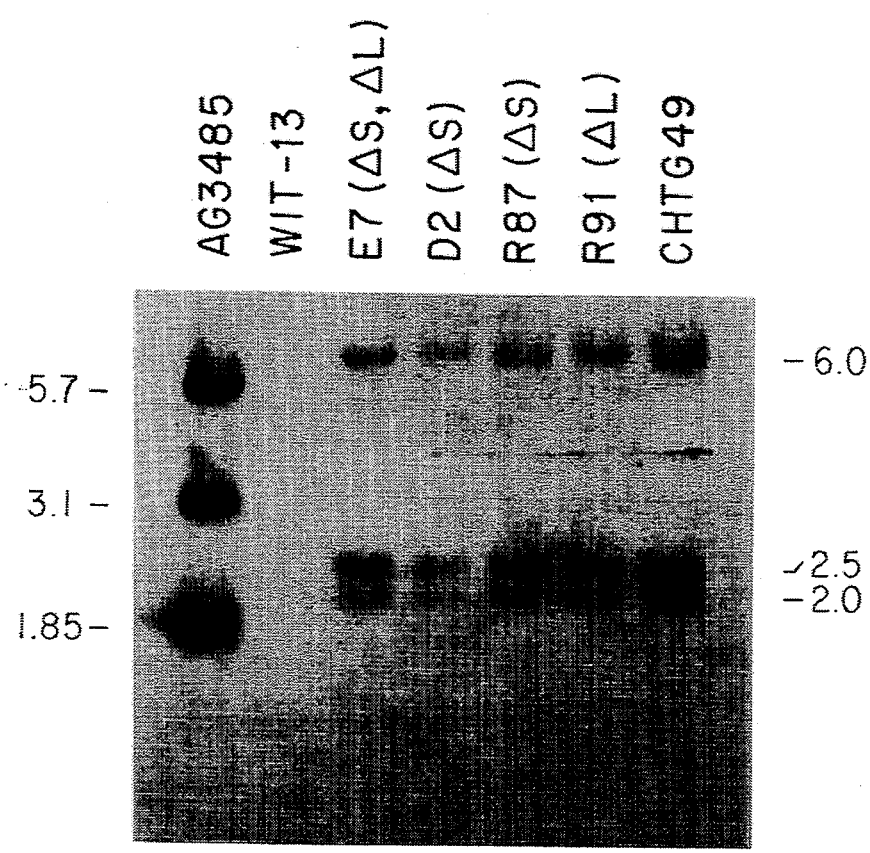
FIG. 6B shows the results of Southern blot analysis of Wit-13 hybrid cell lines digested with Eco RI and hybridized with WT2.

The relationship between cDNA clones isolated as described and genomic DNA sequences in 11p13 was also assessed, as described in detail in the Examplification. Briefly, segments of the WT33 cDNA were hybridized to genomic DNA from diploid human cell lines and to a panel of somatic cell hybrids which permits fine structure mapping within 11p13 (Table). As shown in FIG. 6A, WT33 cDNA hybridizes to seven EcoRI fragments in normal human DNA which are 13.5, 10.4, 6.1, 5.7, 3.7, 3.1, and 1.85 kb in length. Analysis of somatic cell hybrids confirmed that all of these restriction fragments are located on chromosome 11 in band p13. Furthermore, these DNA sequences are all homozygously deleted from cell line WiT-13 and hybrids derived from this line. (FIG. 6B and data not shown).

Figure 7:
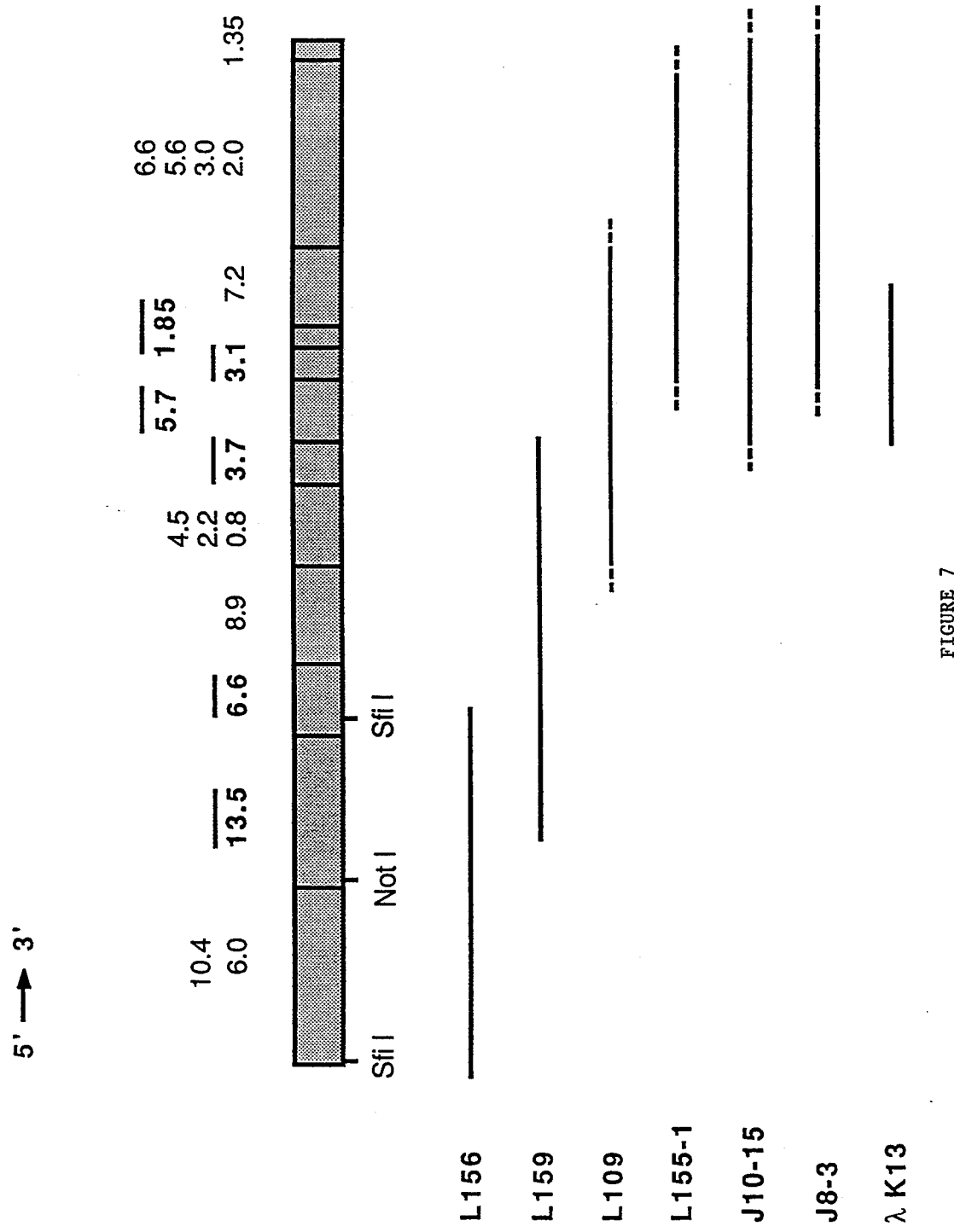
FIG. 7 shows the genomic organization of six overlapping cosmids encoding the WT33 mRNA; a composite Eco RI restriction map of the 93 Kbp genomic region spanning the WT33 cDNA is shown at the top of the Figure.

To further analyze the structure of the genomic DNA within the region, WT33 was used as a probe to isolate additional cosmid DNA clones. FIG. 7 shows a composite map of four cosmids derived from this analysis (L156, L159, L109, L155-1) plus the two original cosmids, J8-3 and J10-15, and phage clone λK13. Glaser. T., The fine structure and evolution of the eleventh human chromosome. Ph. D. thesis, Massachusetts Institute of Technology, Cambridge, Mass. (1988). The cloned genomic sequences span a DNA segment greater than 90 kb in length. To relate genomic and cDNA clones, an Eco RI digest of each cosmid was hybridized with segments of WT33 cDNA. In this manner, all seven Eco RI fragments observed by Southern hybridization of the cDNA to genomic DNA were identified within this collection of overlapping clones (FIG. 7) Orientation of the transcriptional unit was established by hybridizing restriction digests of each cosmid with probes derived from different subregions of the WT33 cDNA. (See the Exemplification). These data indicate that the WT33 transcriptional unit must extend from a position close to the Not I site in cosmid L156 and continue in the 3' direction, extending through the 1.85 kb Eco RI fragment common to cosmids L109, L155-1, J10-15, J8-3 and clone λK13. These hybridizing Eco RI fragments span approximately 50 kb. Since WT33 cDNA is not full length (See above),the entire gene may be greater in size than 50 kb.

An analysis of restriction enzyme recognition sites in cloned genomic DNA permits a direct comparison to the pulsed field gel electrophoresis map of the region. As shown in FIG. 7, the 5' end of the genomic DNA segment encoding the 5' end of WT 33 cDNA includes a recognition site for the restriction enzyme Not I. Pulsed field gel mapping demonstrates that the 11p13 Wilms' tumor gene is located within the boundaries of two adjacent Not I fragments, 500 kb and 325 kb in length. Hybridization to genomic DNA digested with both Sfi I and Not I confirms that the Not I site in cosmid L156 represents the junction between the 325 kb and 500 kb Not I restriction fragments. Since pulsed field gel analysis places the 500 kb Not I fragment centromeric to the 325 kb Not I fragment, transcription must proceed in a centromeric to telomeric direction.

Cosmid L156 contains sites for a number of restriction enzymes with recognition sequences which contain the dinucleotide CpG, including Not I, BssH II and Eag I. These data, as well as pulsed field gel analysis, indicate the presence of an "HTF island" in the region of genomic DNA surrounding the Not I site. HTF islands are frequently located at the 5' ends of transcription units, Bird, A. et al., *Cell*, 40:91–99 (1985); Bird, A., *Nature*, 321:209–213 (1986); Lindsay, S. and A. P. bird, *Nature*, 327:336 (1987), suggesting that the genomic DNA is cosmid L156 may contain the 5'end of the WT33 transcription unit.

Figure 8A:
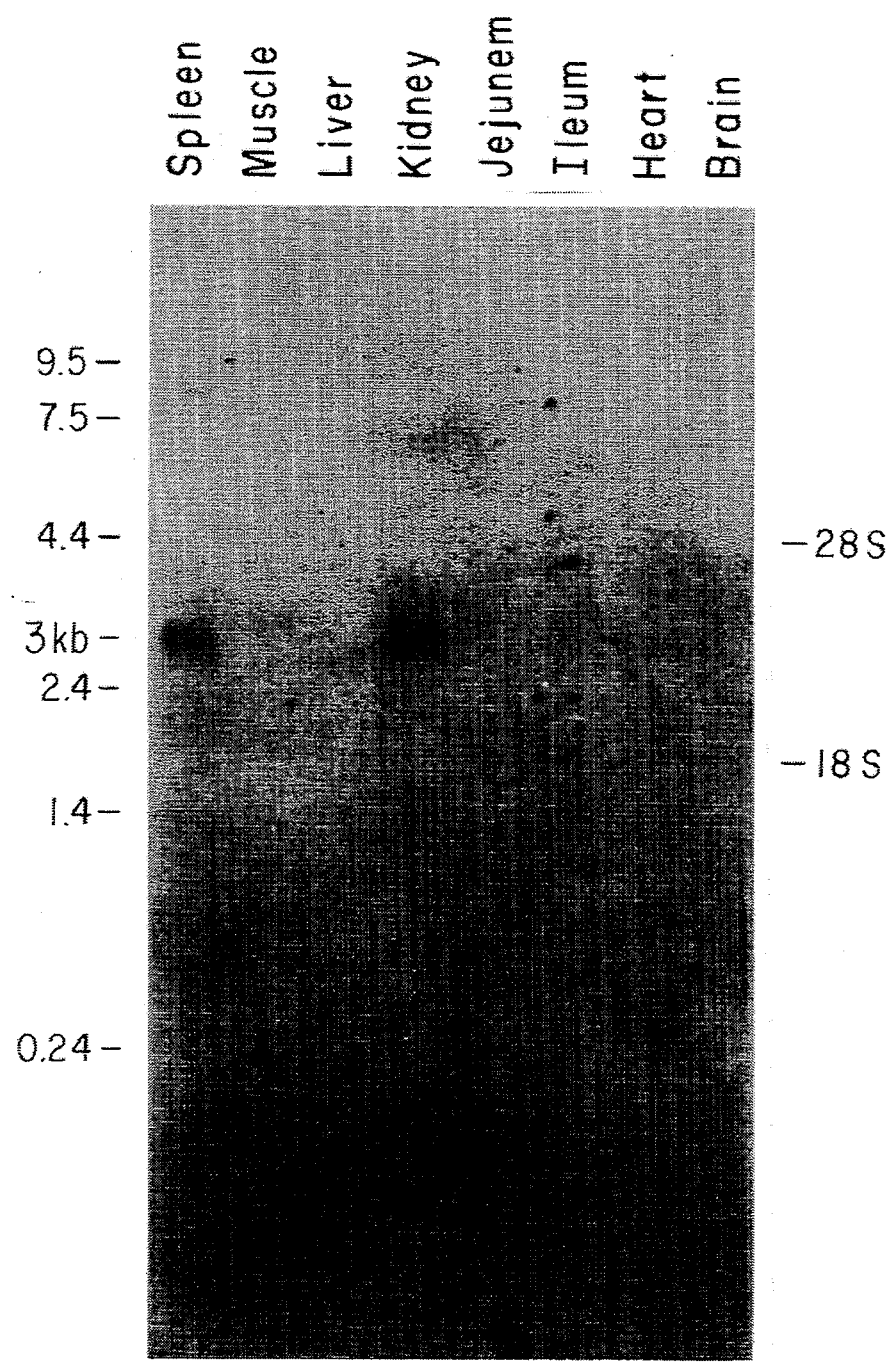
FIG. 8A shows the results of Northern blot analysis of the tissue specific expression of WT33 in baboon.
Figure 8B:
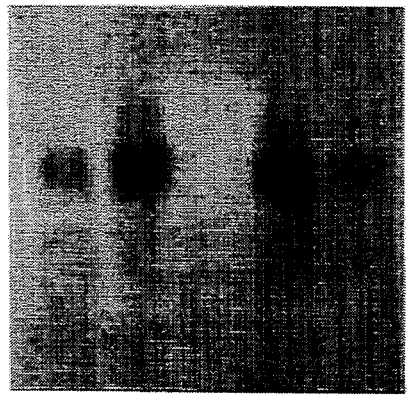
FIG. 8B shows the results of Northern blot analysis of the tissue specific distribution of RNA from mouse and baboon tissues.

The size and tissue distribution of the WT33 transcript(s), were also assessed, by performing a series of Northern blotting experiments. FIG. 8A shows the hybridization of WT33 cDNA to total cellular RNA isolated from a variety of baboon tissues. A mRNA species approximately 3 kb in length is detected in baboon kidney and spleen RNA. A faint hybridization band at 3 kb is also observed in heart upon long exposure (FIG. 8B), while no detectable hybridization is observed in RNA derived from muscle, liver, jejunum, ileum or brain (FIG. 8A). WT33 is an effective probe in hybridization to RNA derived from mouse tissues as well. A 3 kb mRNA species homologous to WT33 is observed in mouse tissues as well. A 3 kb mRNA species homologous to WT33 is observed in mouse kidney (FIG. 8B). The tissue specific expression pattern of WT33 mRNA in the adult mouse is similar to the baboon. Developmental studies in the mouse show that the WT33 mRNA is most highly expressed in fetal kidney. This expression is consistent with a gene capable of growth regulation in the metanephric blastema, the presumed tissue of origin for Wilms' tumor. Bove and McAdams, (1976) ibid. The finding of homology with the EGR1 and EGR2 genes also suggests WT33 may exert a role in the growth regulation of nephroblasts.

Figure 8C:
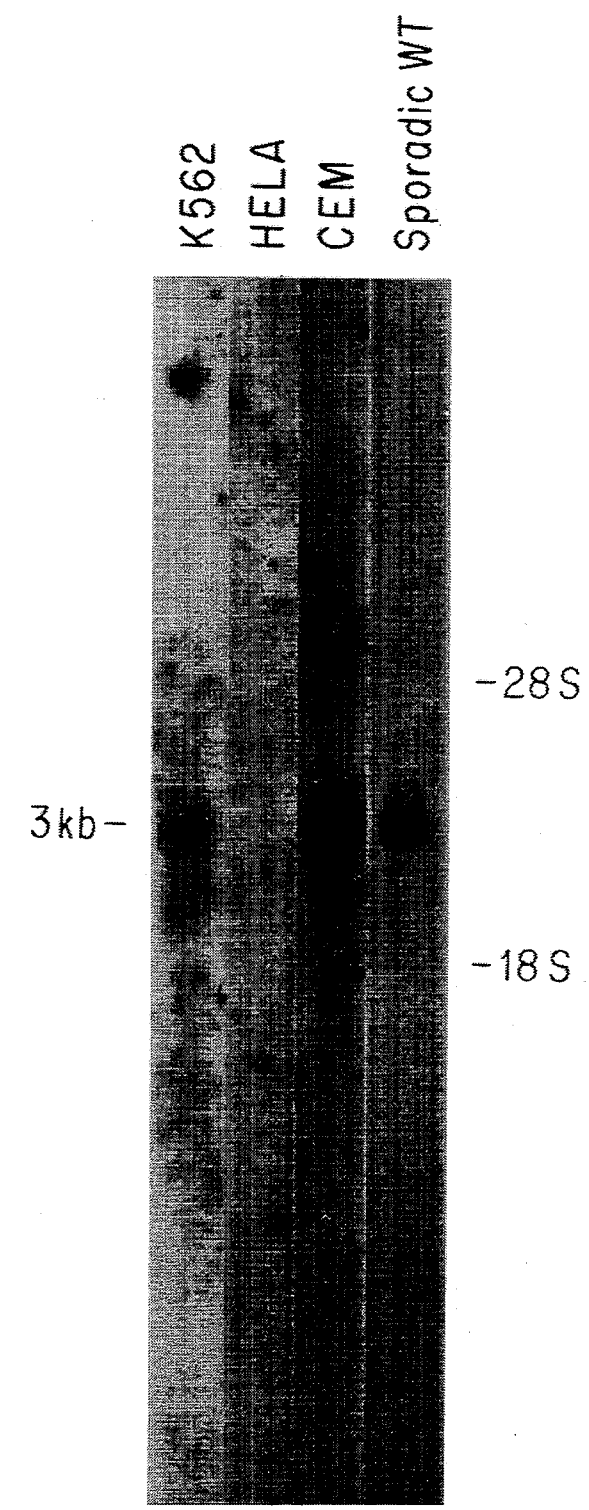
FIG. 8C shows the results of Northern blot analysis of expression of WT33 in tumor cell lines.

A spectrum of tumor cell lines, including two neuroblastomas (SK-N-BE(2) and NGP), a retinoblastoma (WERI) a breast carcinoma (MCF7), two osteosarcomas (HOS and U205) two melanomas (SK-MEL-130 and SK-MEL-147) a bladder carcinoma (Ej), two colon carcinomas (SE480 and WIDR), a cervical carcinoma (HeLa) and two Epstein-Barr virus transformed B cell lines (TSH-1 and TSH-2) did not show detectable hybridization to WT33 cDNA. In contrast, RNA isolated from several sporadic Wilms' tumors showed strong hybridization to WT33 cDNA at the 3 kb position. An example is shown in FIG. 8C. Similarly, RNA isolated from two hematopoietic cell lines, an erythroleukemia (K562) and an acute lymphocytic leukemia (CEM), also showed strong hybridization to WT33 at the 3 kb position (FIG 8C).

Results demonstrated expression of the WT33 transcript in cells of kidney and a subset of hematopoietic cell lines. These results are consistent with the tissue specific expression observed predominantly in the baboon kidney and spleen.

Thus, using the method described, DNA which corresponds to the Wilms' tumor gene was identified, isolated and sequenced. The DNA has been shown to encode a transcription unit which spans approximately 50 kb and encodes an mRNA approximately 3 kb in length. This mRNA is expressed in a limited range of cell types, predominantly in the kidney and a subset of hematopoietic cells. The polypeptide encoded by this locus has a number of features which suggest a potential role in the regulation of transcription. These include the presence of four zinc finger domains and a region rich in proline and glutamine. The amino acid sequence of the predicted polypeptide shows significant homology to two growth regulated mammalian polypeptides EGR1 and EGR2. The genetic localization of this gene, its tissue-specific expression, and the function predicted from its sequence indicate that it represents the 11p13 Wilms' tumor gene.

As a result of the isolation and characterization of the Wilms' tumor gene, a method by which samples can be analyzed for the Wilms' tumor gene or a representative portion of the gene is available, as are reagents (e.g., nucleic acid probes antibodies) useful in the method. This method can be used for diagnostic purposes, such as in assessing the likelihood/risk of development of WAGR syndrome and/or Wilms' tumors and in determining in an individual who presents with symptoms associated with or possibly indicative of WAGR or Wilms' tumor whether the disease is present or not. For example, cells obtained from an individual can be probed with all or a portion of the nucleotide sequence represented in FIG. 3, using known techniques. The nucleotide sequence of such a probe need not be precisely the same as that in FIG. 3. It need be only sufficiently similar to the sequence of FIG. 3 that it will hybridize to the Wilms' tumor gene under the conditions used. Cells (e.g., blood, kidney) can be obtained prenatally or postnatally and the occurrence of the Wilms' tumor gene assessed. Cells can be analyzed for the Wilms' tumor DNA, the encoded RNA transcript and/or polypeptides encoded by the Wilms' tumor gene. For example, cells can be obtained, prenatally or postnatally, and analyzed for Wilms' tumor DNA. This can be carried out using standard blotting techniques, (e.g., Southern blot) and a radioactively labelled DNA probe which hybridizes to (is complementary to) all or a portion of the Wilms' tumor. A radioactively-labelled DNA probe can be combined with cellular DNA previously treated to render it available for hybridization with complementary DNA, under conditions appropriate for hybridization to occur. After sufficient time for the labelled DNA probe and complementary DNA in the sample (if present) to hybridize and form labelled DNA probe/sample DNA complexes, detection of the labelled probe/sample DNA complexes is carried out using known methods (e.g., autoradiography). The label can be any substance which can be detected and whose presence does not interfere with the availability of probe DNA to bind to complementary DNA (e.g., fluorescent material). The method by which labelled DNA probe/sample DNa complexes are detected will depend on the type of label used (e.g., in the case in which a fluorophore is used, fluorescence detection will be used). If necessary, DNA obtained from the sample can be amplified, using a known technique such as the polymerase chain reaction, and the amplified DNA analyzed for the occurrence of Wilms' tumor DNA. If sample DNA is amplified, the product is an amplification mixture which contains amplified DNA of interest (DNA which includes Wilms' tumor DNA) and amplified DNA other than DNA of interest. Generally, DNA in the amplification mixture is separated on the basis of size, using known techniques. The separated amplified DNA is analyzed for DNA of interest using a known technique, such as Southern blotting, DNA sequencing, digestion with appropriate restriction endonuclease or visualization of ethidium bromide stained gels.

Alternatively, mRNA can be detected in the sample obtained, using as a probe all or a portion of the Wilms' tumor gene. This can be carried out using mRNA obtained from an individual's cells, or using mRNA obtained from cells and amplified using a known amplification technique, such as the RNA PCR. In either case, RNA is analyzed using a known technique, such as Northern blotting. Antibodies specific for the Wilms' tumor gene-encoded polypeptide (or a polypeptide portion) can also be used for diagnostic purposes. Such antibodies can be produced using known techniques or obtained commercially. Maniatis, T. et al., *Molecular Cloning: A Laboratory Manual*, Cold Spring Harbor (1982). In this embodiment, antibodies specific for the polypeptide encoded by the Wilms' tumor gene (e.g., as encoded by all or a portion of the sequence of FIG. 3 or its functional equivalent) are combined with a sample (e.g., kidney cells, blood cells) obtained from an individual. The antibody used can be delectably labelled (e.g., with a radioactive or fluorescent material). After sufficient time for polypeptide present in the sample and antibody to combine or bind, to form Wilms' tumor gene-encoded polypeptide/specific antibody complexes, the occurrence (presence or absence and/or quantity) of complexes is determined, using known techniques. If labelled specific antibody is used, the occurrence of labelled complexes is determined (e.g., by autoradiography, fluorescence detection). Alternatively, the sample can be combined with a solid support (e.g., nitrocellulose, glass slide, polystyrene beads, immunomagnetic beads) which bears an antibody specific for the antibody present in the complex. This results in binding of specific antibody in the sample (e.g., in the polypeptide/specific antibody complexes) to the solid support. The resulting solid support-bound complex can be removed from the sample and detected using known techniques. For example, if the antibody in the Wilms' tumor gene-encoded polypeptide/specific antibody complex is labelled, detection of the support-bound complex is carried out by detecting the label.

The present method is useful for early detection of WAGR and Wilms' tumor and, as a result, earlier intervention, in the form of surgery, chemotherapy and/or radiation therapy, will be possible. For example, the present method can be used to diagnose this condition in a patient who has an enlarging abdominal mass, abdominal pain, hematuria or constitutional symptoms (e.g., fever, vomiting, poor appetite, malaise, polycythemia, hypertension) suggestive of Wilms' tumor. That individual can, after diagnosis through use of the present method, be treated as described.

The present method of detecting the Wilms' tumor gene can also be used to identify in other tumor types a lesion which is the same as or similar to the lesions which occur in the case of Wilms' tumor. That is, it is reasonable to expect that the Wilms' tumor gene (i.e., the DNA sequence referred to herein as the Wilms' tumor gene) or a closely-related gene is expressed in other tumor types (e.g., leukemia cells, testicular tumor) and that it is causally associated with those tumor types or serves as a reliable indicator (marker) of such tumor types, although perhaps not directly or solely responsible for formation of a particular type of tumor. Thus, the present method and appropriate reagents, such as DNA sequences within the cosmid clones described herein or the Wilms' tumor gene itself, can be used to identify in other tumor types similar lesions in chromosome 11 band 13. The DNA sequences described herein can be used to identify in a tumor sample (e.g., leukemia cells, testicular tumor) an altered 11p13 sequence, using known techniques and the method described herein.

The invention will now be illustrated further by the following Exemplification.

EXEMPLIFICATION

Materials and Methods

Cell Culture

Somatic cell hybrids were isolated containing chromosome 11 or translocation chromosomes from patient cell lines DG-85-1436 and GM4613. DG85-1436 is a fibroblast cell line derived from a patient with familial aniridia involving a cytologically balanced translocation of chromosome 11 and 22 [t(11;22)(p13;q12.2)]. Moore et al., *Hum. Genet.*, 72:297–302 (1986). GM4613 is a fibroblast cell line (Human Genetic Mutant Cell Repository, Camden, N.J.) exhibiting a cytologically balanced translocation involving chromosome 2 and 11 (t(2;11)(p11; p13)) derived from a neonate with Potter syndrome. Potter, *In Normal and Abnormal Development of the Kidney*, Year Book Medical Publ., Chicago, Ill., pp. 3–79, 83–123 and 259–281 (1972). Somatic cell hybrids were isolated as previously described. Glaser et al., *Nature*, 321:282–887 (1986). The chromosome 11 haplotype of these hybrids was determined by RFLP analyses with DNA probes on both the short and long arms of chromosome 11. All initial DG hybrids retained the der (11), der (22), and the normal chromosome 11. Cell surface antigen studies revealed that a minor subpopulation of one hybrid, DG-7A-3, possessed only the der (22) chromosome. Two hybrids R19-2C and R19-3B, possessing only the der (22) chromosome were isolated by cell surface antigen selection from the DG-7A-3 population. This was accompanied by selecting for retention of the mer2 surface antigen in 11p15 and selecting against the MIC1 surface antigen centromeric to the translocation in 11p13. In the case of the Potter patient, GM4613 hybrids which retained only the der (11) (BW G2-5), the der 2 (BW A2-5) or the normal 11 chromosome (BW H2-3) were identified by RFLP analysis.

Patient HV has familial aniridia associated with a cytologically balanced translocation involving chromosome 11 and 4 t(4;11)(q22; p13), as described by Simola and Simdu et al., *Hum. Genet.*, 63:158–161 (1983). HV human-mouse hybrid R195 contains the der (11) chromosome and HV hybrid LHV-1A5 contains the der (4) chromosome. Hybrids from WAGR patients JH, MH and NW, have been described. Glaser et al., *Nature*, 321:882-887 (1986). Mouse-human hybrid 15.14 hybrid from Wilms' tumor patient DR with an interstitial deletion of 11p13-p12 (Turleau et al., *Hum. Genet.*, 67:455–456 (1986)) has been characterized). Genomic DNA from this cell line was kindly provided by Dr. Claudine Junien (INSERM, Paris). Cell line WIT-13 was derived from xenograph cultures of a stage III Wilms' tumor with classical triphasic histology; the tumor arose sporadically in an otherwise healthy two year old female. Lewis et al., *Genomics*, 3:25–31 (1988).

Isolation of Cosmid Clones

High molecular weight DNA was prepared from the J1-11 hybrid, a Chinese hamster-human somatic cell hybrid possessing only the short arm of human chromosome 11. Kao et al., *Proc. Natl. Acad. Sci. USA*, 73:193–197 (1976). This DNA was used to construct cosmid libraries in the vectors pJB8 (Ish-Horowitz and Burke *Nucl. Acid Res.*,9:2989–2998 (1981)) and pWe15 according to the method of Evans and Wahl. Evans and Wahl, *Methods In Enzym.*, 152:604–610 (1987). DNA was partially digested with the restriction enzyme Mbo I and fragments of 35 to 45 kb were isolated using a 5-25% NaCl gradient. This DNA was ligated to vector DNA and packaged as λ phage (Gigapack Gold, Stratagene, La Jolla, Calif.) which were used to infect *E. coli* strains 1046 or DH5. Colonies were plated at a low density (1,000 to 2,000 per 150 mm plate) on LB-ampicillin plates. Maniatis et al., *In: Molecular Cloning: A Laboratory Manual*, Cold Spring Harbor Laboratory, Cold Spring Harbor, N.Y. (1982).

Screening of Genomic Libraries

Standard screening methods were performed, as outlined by Maniatis et al., (1982) ibid. Replica filters were screened for human positives by hybridization with radiolabeled total human DNA (Gusella et al., *Proc. Natl. Acad. Sci. USA*, 77:2829–2833 (1988)), a cloned human Alu repeat probe (Blur 11) (Jelinik et al., *Proc. Natl. Acad. Sci. USA*,77:1398–1402 (1980)) or Cot$_1$ human repeat enriched DNA (Shih and Weinberg, *Cell*, 29:616–619 (1982)). Approximately 0.5–1% of colonies in the J1-11 library were identified as human positive. Cosmid DNA was isolated from small scale cultures of each of these human positive colonies according to Maniatis et al., (1982) ibid. The EcoRI restriction pattern of cosmids was analyzed by standard agarose gel electrophoresis.

Mapping of Cosmids

An abbreviated mapping panel of J1 cell hybrids possessing defined segments of human chromosome 11p was used to rapidly identify human cosmids in 11p13. Human cosmids were mapped by preannealing radiolabelled DNA with total sheared human DNA to minimize signal from human repeats (Litt and White, *Proc. Natl. Acad. Sci. USA*, 82:6206–6210 (1985)) and hybridizing with a nylon (Zetabind, AMF-Cuno) filter of Eco RI digested DNA from J1 cell hybrid.

Isolation of Single Copy Sequences

Single copy sequences were subcloned from cosmids as follows. Cosmids were digested to completion with Sau3A I and the resulting fragments subcloned into the Bam HI polylinker site of the plasmid pUC19. Clones with inserts were gridded on nitrocellulose filters and those with single copy sequences were identified by lack of hybridization to repeat enriched (Cot$_1$) DNA. Random single copy fragments were further tested by hybridizing radiolabelled inserts isolated from low melt agarose gel slices to nitrocellulose filters of human and λ phage DNA. Probes J7-18p2 and J8-3p4 were among the single copy sequences identified from these cosmids.

Origin of DNA Probes

Human cosmids J7-18, J8-3 and J10-15 were isolated from the J1-11/pWe15 cosmid library. Four additional cosmids (L156, L159, L155-1, L109) were isolated from a total human pWe15 cosmid library (Stratagene, La Jolla. Calif.) using a 1.8 kb Eco RI fragment of the WT33 cDNA as a probe. The localization of all cosmids to 11p13 was verified by somatic cell mapping. Genomic probes J7-18p2 and J8-3p4 were identified as 0.5 kb and 1.3 kb single copy Eco RI/HindIII fragments in pUC19 from cosmids J7-18 and J8-3, respectively. Phage λK13 was isolated from a λ dash (Stratagene) library constructed from a BamHI complete digest of Goss-Harris hybrid 3A. The CAT probe is a 0.6 kb PstI-AvaI fragment of the cDNA clone pC24. Bruno et al., *Am. J. Hum. Genet.*, 36:245 (1984). The FSHB probe is a 1.4 kb PstI insert of pFSH-1.4. Watkins et al., *DNA*, 6:205–212 (1987).

Southern Blots

Isolation and digestion of genomic DNA, transfer of DNA to nylon membranes, hybridization of radiolabelled probe, washing of filters, and autoradiography were performed as outlined by Glaser et al., (1986) ibid. DNA was radiolabeled with $^{32}$P-αdCTP (New England Nuclear) according to the random primer method. Feinberg and Vogelstein, *Biochem. Biophys. Res. Comm.*, 111:47–54 (1983).

Screening of cDNA Libraries

Human cDNA libraries of embryonic kidney, adult kidney and pre-B cell origin were screened. Maniatis et al., (1982) ibid. For screening each library, a total of 10$^6$ phage were plated on NZCYM agarose plates and two replicas of each plate were made with nitrocellulose filters. Schleicher and Schull. The replica filters were treated with denaturing solution, neutralizing solution and 2X SCC (1X SCC=0.15M NACl, 0.015M Na citrate) for 5 min. each and then baked at 80° C. in a vacuum oven for 2 hours according to Maniatis et al., (1982) ibid. Replica filters were hybridized with the conserved single copy probe, j8-3p4, or with subfragments of WT cDNAs.

Northern Blots

Total RNA was isolated by a LiCl/urea procedure. Auffray and Rougeon, *Eur. J. Biochem.* 107:303–314 (1980). Cells were harvested, pelleted, resuspended in 3M LiCl/6M urea and homogenized at 4° C. RNA was precipitated, washed in 3M LiCl/6M urea, precipitated and resuspended in TE/SDS. RNA was extracted in phenolchloroform (2–3 x), ethanol precipitated, lyophilized, resuspended, quantitated and stored at −20° C. 10–20 μg of RNA was run on a 1% agarose 37% formaldehyde RNA gel and blotted on Gene Screen Plus (New England Biolabs) membrane. The filters were prehybridized and hybridized at 42° C for 24 hours in 50% formamide, 5 x Denhardts solution, 0.5% SDS (sodium dodecyl sulfate), 10% dextran sulfate, 0.1% pyrophosphate and 100 μg/ml salmon sperm DNA. Blots were hybridized with a conserved genomic probe J8-3p4, cDNA 2-1 (1.5 kb Pst I/Eco RI fragment), a 0.5 kb Sau3a I subclone of cDNA 2-1 or a 1.8 kb Eco RI fragment of the cDNA WT33. After an 18–36 hour hybridization, blots were washed twice in 2xSSC. 0.1% SDS for 30 minutes at room temperature and one to two times in 1xSSC. 0.1% SDS for 30 minutes at 55°–60° C.

DNA Sequencing

DNA sequencing was done by chain termination, Sanger et al., *Proc. Natl. Acad. Sci. USA*, 74:5463–5467 (1977) using double stranded DNA templates. Restriction fragments of the WT33 cDNA were subcloned into pUC19 or Bluescript (New England Biolabs). Direct sequencing primers for Bluescript were obtained from New England Biolabs. Additional oligonucleotide primers (synthesized by Research Genetics, Huntsville, Ala.), corresponding to the cDNA were also used for sequencing the cDNAs. The WT33 cDNA was sequenced on both strands. In addition, sequence was confirmed on regions of other cDNAs (WT2, WT4 and WT22). Sequencing reactions were electrophoresed on 6% and 8% polyacrylamide gels, dried and autoradiographed. Using the Fast-P algorithm. Lipman and Pearson, *Science*, 227:1435–1441 (1985), the predicted amino acid sequence of the cDNA WT33 was compared with protein sequences stored in the National Biomedical Research Foundation Protein Identification Resource (NBRF/PIR data base).

RESULTS

Isolation and Mapping of Genomic Probes

A cosmid library was constructed from a hybrid cell line, J1-11, in which the short arm of chromosome 11 had been segregated from the remainder of the human genome in a Chinese hamster background. Kao et al., (1976) ibid. A total of 119 cosmid clones containing human DNA sequences were isolated, all of which mapped to the short arm of chromosome 11. To identify clones within the WAGR region, a mapping panel of somatic cell hubrids containing different fragments of human chromosome lip was used. Glaser et al., (1989) ibid. Three cosmids, J7-18, J8-3 and J10-15, appeared to map the closest to the region containing the Wilms' tumor gene. The restriction maps of cosmids J8-3 and J10-15 showed substantial overlap. Hence, single copy sequences (J7-18p2 and J8-3p4) were subcloned and identified from cosmids J7-18 and J8-3, respectively.

The fine localization of these single copy DNA sequences within 11p13 was determined by hybridization to a series of somatic cell hybrids derived from patients with translocations and deletions which define specific intervals within the WAGR region. Subclones J7-18p2 and J8-3p4 were hybridized to DNA from hybrid cells derived from an aniridia patient DG. This patient has a cytogenetically balanced 11;22 translocation which bisects band 11p13. The translocation was inherited with aniridia for several generations in this family, Moore et al., (1986) ibid., and is associated with a small molecular deletion at the breadpoint. Davis et al., (1988b) ibid.; Gessler et al., (1989b) ibid. Human DNA sequences homologous to probes J7-18p2 and J8-3p4 were shown to be absent in cell lines R19-2C and R19-3B, which contain only the derivative (der) (22) chromosome. These results, and a normal gene dosage in fibroblast DNA from this patient, place J7-18p2 and J8-3p4 on the centromeric side of the DG translocation breakpoint on chromosome 11. Analogous results were obtained with hybrid cells derived from a second unrelated aniridia patient (HV) also carrying an 11p13 translocation (Table). Accordingly, both cosmids map centromeric to AN2, towards the Wilms' tumor locus.

TABLE

Mapping of 11p13 probes using Patient Hybrids

| Phenotype | Patient | Hybrid | Chromosome 11 Content | Probe J7-18p12 | J8-3p4 | cDNA |
|---|---|---|---|---|---|---|
| Aniridia | DG | R19-2C | der(22) | − | − | − |
|  | HV | R195 | der(11) | ND | + | + |
|  | HV | LHV-1A5 | der(4) | − | − | − |
| Urogenital Defects | BW | H2-3 | N1(11) | + | + | + |
|  | BW | G2-5 | der(11) | − | − | − |
|  | BW | A2-5 | der(2) | + | + | + |
| WAGR | JH | C/h | del(11p14.1-p11.2) | − | − | − |
|  | NW | F3 | del(11p13) | − | − | − |
|  | MJ | A9 | del(11p13) | − | − | − |
| WT (constitutional) | DR | 15.14 | del(11)p13-p12) | + | − | − |
| WT (sporadic) | WiT-13 | D2 & R87 | del(11)pΔS) | + | − | − |
|  | WiT-13 | R91 | del(11)pΔL) | − | − | − |

Hybridization of J7-18p2 to DNA from somatic cell hybrids derived from a second patient (BW), an individual with multiple urogenital defects (Potter's syndrome) and a (t(2;11)(p11; p13) translocation (GM4613Human Genetic Mutant Cell Repository, Camden, N.J.) was hybridized to J7-18p2 and J8-3p4. The breakpoint of this translocation identifies the site of a potential genetic determinant of genitourinary abnormalities. Porteus et al., (1987) ibid. Both probes hybridize to cell line A2-5, containing the der (2) chromosome and fail to hybridize to cell line G2-5, containing the der (11) chromosome. Therefore, both are located between the aniridia and Potter translocation breakpoints. Since this interval contains the Wilms' tumor gene, these findings suggest that J7-18p2 and J8-3p4 are close to or within the Wilms' tumor locus.

Analysis of chromosome 11 deletions from WAGR and Wilms' tumor patients (Table) permits more precise localization of these probes in relation to the Wilm's tumor gene. Both J7-18p2 and J8-3p4 are hemizygously deleted in three constitution WAGR deletions (patients JH, MJ and NW) tested, consistent with the positioning of these DNA sequences in close proximity to the Wilm's tumor locus.

The position of J7-18p2 and J8-3p4 relative to the Wilms' tumor locus was further investigated by hybridization to DNA from cell lines derived from two Wilms' tumor patients. Patient DR is an individual with a constitutional deletion of 11p12-p13, Couillin et al., (1988) ibid., terminating between the Wilms' tumor and AN2 loci (Table). J7-18p2 is present in the deleted chromosome 11 of patient DR, whereas J8-3p4 is absent (Table). Since catalase is deleted in DR, J7-18p2 must be telomeric to J8-3p4. The distance between these two probes is less than 340 kb. The DR data indicates that the distal boundary of the region which must contain the Wilm's tumor patient Wit-13 has previously been shown. Lewis et al. (1988) ibid., to carry overlapping 11p13 deletions in tumor tissue, as demonstrated by the homozygous deletion of the anonymous DNA segment D11S87. Since J7-18p2 is present in this chromosome, but J8-3p4 is absent (Table 1), the $\Delta_S$ (small) deletion chromosome 11 of Wit-13 must have a breakpoint between the two probes. J8-3p4 is homozygously deleted in Wit-13 since it also was found to be absent in the $\Delta_L$ (large) deletion chromosome. The proximal limit to the position of the Wilms' tumor locus is the endpoint of the $\Delta_L$ deletion on WIT-13. The finding that J8-3p4 is homozygously deleted in WiT-13, thus maps it to the 11p13 region containing the Wilm's tumor locus, an interval which is 345 kb or less based on analysis by pulsed field gel electrophoresis (Rose et al., submitted). A map summarizing these findings is shown in FIG. 2.

Isolation of cDNA Clones

Figure 4:
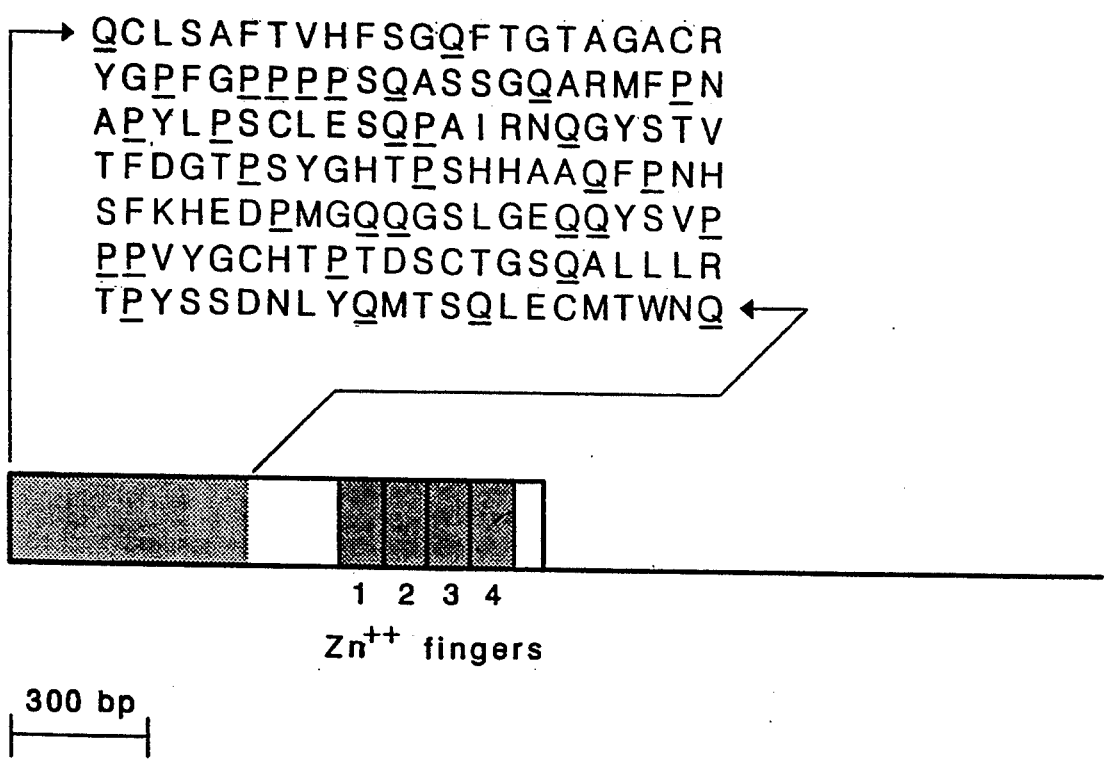
FIG. 4 is a schematic map of the WT33 cDNA; the open reading frame is shown in the boxed region and the deduced amino acid sequence of the proline/glutamine rich region appears above the shaded open reading frame.

The map position of J8-3p4 indicated that this probe was close to or within the Wilm's tumor locus. Two observations suggested that J8-3p4 contained a portion of a transcription unit. First, strong cross-species hybridization to hamster and mouse DNA genomic sequences was observed in somatic cell hybrids with J8-3p4 (FIGS. 1A and 1B). Cross species conservation is often associated with expressed DNA sequences. Second, J8-3p4 showed hybridization to RNA isolated from baboon kidney and spleen. J8-3p4 was used as a probe to screen a cDNA library derived from human embryonic kidney (HEK) cells. On the basis of Northern blotting results, a human adult kidney and a human pre B cell library were also screened. Four cDNA clones, two from HEK (WT4, WT2) one from human adult kidney (WT22) and one from a pre B cell line (WT33), were studied in detail. Using another independently isolated conserved genomic DNA clone, $\lambda$K13, a fifth homologous cDNA clone (WT13) was also isolated from the HEK library. The longest cDNA clone isolated, WT33, is 2313 base pairs in length (FIGS. 3 and 4). The WT33 cDNA extends the furthest in both the 5' and 3' directions. The other four cDNAs share a common internal region of DNA sequence approximately 1000 to 1200 base pairs in length.

Sequence Analysis of the WT33 cDNA

The nucleotide sequence of the WT33 cDNA was determined and the predicted amino acid sequence was derived. The sequence of WT33 reveals a continuous open reading frame of 345 amino acids which extends from nucleotide 1 to 1035. A schematic representation of the WT33 cDNA is illustrated in FIG. 3. This open reading frame represents most of the WT33 coding segment, but it does not include the initiator methonine codon. Primer extension experiments suggest that an additional 200 bp are present at the 5' end of the mRNA corresponding to WT33. The transcription pattern of the locus corresponding to WT33. The transcription pattern of the locus corresponding to these cDNAs exhibits some complexity. Experiments utilizing RNA PCR (polymerase chain reaction) indicate variation in mRNA sequence in the 5' segment of the coding region of the mRNA, suggesting alternative splicing patterns among various tissue types.

Of particular interest, nucleotides 670 to 1002 encode four contiguous "zinc finger" domains. The zinc finger motif was first described in Xenopus TF-IIIA which binds to DNA in the internal control region of the 5 S genes. Miller et al., *EMBO. J.*, 4:1609–1614 (1985); Brown et al., *FEBS Lett.*, 186:271–274 (1985). Subsequently, other nucleic acid recognizing proteins have been reported to contain the zinc finger domain. Klug and Rhodes, *TIBS*, 12:464 (1987); Evans and Hollenberg, *Cell*, 52:1–3 (1988). The zinc finger sequence motif consists of a repeating unit of 29–30 amino acids (Y/F-X-C-$X_{2-4}$-C-$X_3$-F-$X_5$-L-$X_2$-H-$X_{3-4}$-H-$X_{6.7}$, where X is any amino acid) which folds into a domain chelating a zinc atom between a pair of cysteines and histidines. Diakun et al., *Nature*, 324:698–699 (1986); Green and Berg, *Proc. Nat'l Acad. Sci. USA*, 86:4047–4051 (1989). All four zinc fingers encoded by WT33 (FIGS. 4 and 5) fit the consensus sequence for zinc fingers. The H/C link between zinc fingers, typified by the amino acid sequence TGE-R/K-P-F/Y-X. Sub et al., *Cell*, 47:1025–1032 (1986), is also conserved in the deduced amino acid sequence of WT33.

EQUIVALENTS

Those skilled in the art will recognize or be able to ascertain, using no more than routine experimentation, many equivalents to the specific embodiments of the invention described herein. Such equivalents are intended to be encompassed within the scope of this invention.

We claim:

1. Isolated DNA consisting essentially of the 11p13 Wilm's tumor gene having the nucleotide sequence as shown in FIG. 3.

2. Isolated DNA which encodes a polypeptide of approximately 345 amino acid residues, the DNA consisting of the nucleotide sequence as shown in FIG. 3.

3. A DNA probe which hybridizes with Wilm's tumor DNA, wherein the probe consists of a sufficient portion of the nucleotide sequence as shown in FIG. 3 to bind preferentially to the Wilm's tumor DNA.

4. A DNA probe which hybridizes with Wilm's tumor RNA, wherein the probe consists of a sufficient portion of the nucleotide sequence as shown in FIG. 3 to bind preferentially to the Wilm's tumor RNA.

5. A kit for detecting Wilm's tumor DNA in a cell, comprising:
   a) a DNA probe which hybridizes with Wilm's tumor DNA, wherein the probe consisting of a sufficient portion of the nucleotide sequence of FIG. 3 to bind preferentially to Wilm's tumor DNA; and
   b) a container.

6. The DNA probe of claim 3 wherein the probe is detectably labeled.

7. A kit for detecting alterations of the Wilm's tumor gene in an individual comprising:
   a) at least one probe, which hybridizes with Wilm's tumor DNA or Wilm's tumor RNA, wherein the probe consisting of a sufficient portion of the nucleotide sequence as shown in FIG. 3 to bind preferentially to the Wilm's tumor DNA or Wilm's tumor RNA; and
   b) a container.

8. The kit of claim 7, wherein the probe is detectably labelled.

* * * * *

UNITED STATES PATENT AND TRADEMARK OFFICE
CERTIFICATE OF CORRECTION

Page 1 of 2

PATENT NO. : 5,350,840
DATED : September 27, 1994
INVENTOR(S) : Katherine M. Call, Thomas M. Glaser, Caryn Y. Ito, Alan J. Buckler, Jerry Pelletier, Daniel A. Haber & Elise A. Rose It is certified that error appears in the above-indentified patent and that said Letters Patent is hereby corrected as shown below:

Delete Drawing Sheet 3 showing incorrect Figure 3 and replace with the corrected Figure 3 shown below.

```
   1  GAGGAGCAGTGCCTGAGCGCCTTCACTGTCCACTTTTCCGGCCAGTTCACTGGCACAGCC
   1   E   E  [Q]  C   L   S   A   F   T   V   H   F   S   G  [Q]  F   T   G   T   A
  61  GGAGCCTGTCGCTACGGGCCCTTCGGTCCTCCTCCGCCCAGCCAGGCGTCATCCGGCCAG
  21   G   A   C   R   Y   G  [P]  F   G  [P   P   P   P]  S  [Q]  A   S   S   G  [Q]
 121  GCCAGGATGTTTCCTAACGCGCCCTACCTGCCCAGCTGCCTCGAGAGCCAGCCCGCTATT
  41   A   R   M   F  [P]  N   A  [P]  Y   L   P   S   C   L   E   S  [Q] [P]  A   I
 181  CGCAATCAGGGTTACAGCACGGTCACCTTCGACGGGACGCCCAGCTACGGTCACACGCCC
  61   R   N  [Q]  G   Y   S   T   V   T   F   D   G   T  [P]  S   Y   G   H   T  [P]
 241  TCGCACCATGCGGCGCAGTTCCCCAACCACTCATTCAAGCATGAGGATCCCATGGGCCAG
  81   S   H   H   A  [Q]  F  [P]  N   H   S   F   K   H   E   D  [P]  M   G  [Q]
 301  CAGGGCTCGCTGGGTGAGCAGCAGTACTCGGTGCCGCCCCCGGTCTATGGCTGCCACACC
 101  [Q]  G   S   L   G   E  [Q] [Q]  Y   S   V  [P   P   P]  V   Y   G   C   H   T
 361  CCCACCGACAGCTGCACCGGCAGCCAGGCTTTGCTGCTGAGGACGCCCTACAGCAGTGAC
 121   P   T   D   S   C   T   G   S  [Q]  A   L   L   L   R   T  [P]  Y   S   S   D
 421  AATTTATACCAAATGACATCCCAGCTTGAATGCATGACCTGGAATCAGATGAACTTAGGA
 141   N   L   Y  [Q]  M   T   S  [Q]  L   E   C   M   T   W   N  [Q]  M   N   L   G
 481  GCCACCTTAAAGGGCCACAGCACAGGGTACGAGAGCGATAACCACACAACGCCCATCCTC
 161   A   T   L   K   G   H   S   T   G   Y   E   S   D   N   H   T   T   P   I   L
 541  TGCGGAGCCCAATACAGAATACACACGCACGGTGTCTTCAGAGGCATTCAGGATGTGCGA
 181   C   G   A   Q   Y   R   I   H   T   H   G   V   F   R   G   I   Q   D   V   R
 601  CGTGTGCCTGGAGTAGCCCCGACTCTTGTACGGTCGGCATCTGAGACCAGTGAGAAACGC
 201   R   V   P   G   V   A   P   T   L   V   R   S   A   S   E   T   S   E   K   R
 661  CCCTTCATGTGTGCTTACCCAGGCTGCAATAAGAGATATTTTAAGCTGTCCCACTTACAG
 221   P   F   M   C   A   Y   P   G   C   N   K   R   Y   F   K   L   S   H   L   Q
 721  ATGCACAGCAGGAAGCACACTGGTGAGAAACCATACCAGTGTGACTTCAAGGACTGTGAA
 241   M   H   S   R   K   H   I   G   E   K   P   Y   Q   C   D   F   K   D   C   E
 781  CGAAGGTTTTTTCGTTCAGACCAGCTCAAAAGACACCAAAGGAGACATACAGGTGTGAAA
 261   R   R   F   F   R   S   D   Q   L   K   R   H   Q   R   R   H   T   G   V   K
 841  CCATTCCAGTGTAAAACTTGTCAGCGAAAGTTCTCCCGGTCCGACCACCTGAAGACCCAC
 281   P   F   Q   C   L   T   C   Q   R   K   F   S   R   S   N   H   L   K   T   H
 901  ACCAGGACTCATACAGGTGAAAAGCCCTTCAGCTGTCGGTGGCCAAGTTGTCAGAAAAAG
 301   T   R   T   H   I   G   Q   K   P   F   S   C   R   W   P   S   C   Q   K   K
 961  TTTGCCCGGTCAGATGAATTAGTCCGCCATCACAACATGCATCAGAGAAACATGACCAAA
 321   F   A   R   S   D   E   L   V   R   H   H   N   M   H   Q   R   N   M   T   K
1021  CTCCAGCTGGCGCTTTGAGGGGTCTCCCTCGGGGACCGTTCAGTGTCCCAGGCAGCACAG
 341   L   Q   L   A   L
```

UNITED STATES PATENT AND TRADEMARK OFFICE
CERTIFICATE OF CORRECTION

PATENT NO. : 5,350,840
DATED : September 27, 1994
INVENTOR(S) : Katherine M. Call, Thomas M. Glaser, Caryn Y. Ito, Alan J. Buckler, Jerry Pelletier, Daniel A. Haber & Elise A. Rose It is certified that error appears in the above-indentified patent and that said Letters Patent is hereby corrected as shown below:

```
1081 TGTGTGAACTGCTTTCAAGTCTGACTCTCCACTCCTCCTCACTAAAAAGGAAACTTCAGT
1141 TGATCTTCTTCATCCAACTTCCAAGACAAGATACCGGTGCTTCTGGAAACTACCAGGTGT
1201 GCCTGGAAGAGTTGGTCTCTGCCCTGCCTACTTTTAGTTGACTCACAGGCCCTGGAGAAG
1261 CAGCTAACAATGTCTGGTTAGTTAAAAGCCCATTGCCATTTGGTGTGGATTTTCTACTGT
1321 AAGAAGAGCCATAGCTGATCATGTCCCCCTGACCCTTCCCTTCTTTTTTTATGCTCGTTT
1381 TCGCTGGGGATGGAATTATTGTACCATTTTCTATCATGGAATATTTATAGGCCAGGGCAT
1441 GTGTATGTGTCTGCTAATGTAAACTTTGTCATGGTTTCCATTTACTAACAGCAACAGCAA
1501 GAAATAAATCAGAGAGCAAGGCATCGGGGGTGAATCTTGTCTAACATTCCCGAGGTCAGC
1561 CAGGCTGCTAACCTGGAAAGCAGGATGTAGTTCTGCCAGGCAACTTTTAAAGCTCATGCA
1621 TTTCAAGCAGCTGAAGAAAAAATCAGAACTAACCAGTACCTCTGTATAGAAATCTAAAAG
1681 AATTTTACCATTCAGTTAATTCAATGTGAACACTGGCACACTGCTCTTAAGAAACTATGA
1741 AGATCTGAGATTTTTTTGTGTATGTTTTTGACTCTTTTGAGTGGTAATCATATGTGTCTT
1801 TATAGATGTACATACCTCCTTGCACAAATGGAGGGGAATTCATTTTCATCACTGGGAGTG
1861 TCCTTAGTGTATAAAAACCATGCTGGTATATGGCTTCAAGTTGTAAAAATGAAAGTGACT
1921 TTAAAAGAAAATAGGGGATGGTCCAGGATCTCCACTGATAAGACTGTTTTTAAGTAACTT
1981 AAGGACCTTTGGGTCTACAAGTATATGTGAAAAAAATGAGACTTACTGGGTGAGGAAATC
2041 CATTGTTTAAAGATGGTCGTGTGTGTGTGTGTGTGTGTGTGTTGTGTTGTGTTT
2101 TGTTTTTTAAGGGAGGGAATTTATTATTTACCGTTGCTTGAAATTACTGTGTAAATATAT
2161 GTCTGATAATGATTTGCTCTTTGACAACTAAAATTAGGACTGTATAAGTACTAGATGCAT
2221 CACTGGGTGTTGATCTTACAAGATATTGATGATAACACTTAAAATTGTAACCTGCATTTT
2281 TCACTTTGCTCTCAATTAAAGTCTATTCAAAA
```

FIGURE 3

Signed and Sealed this

Eighteenth Day of April, 1995

Attest:

BRUCE LEHMAN

Attesting Officer

Commissioner of Patents and Trademarks